US011375931B2

(12) United States Patent
Snyder et al.

(10) Patent No.: US 11,375,931 B2
(45) Date of Patent: Jul. 5, 2022

(54) NON-INVASIVE TRANSDERMAL SAMPLING AND ANALYSIS DEVICE INCORPORATING AN ELECTROCHEMICAL BIOASSAY

(71) Applicant: Cambridge Medical Technologies LLC, Carson City, NV (US)

(72) Inventors: Helena Woodvine Snyder, Crozet, VA (US); Vikas Bhatia, Gaithersburg, MD (US); John Frederick Currie, Bethesda, MD (US); Emil F. Jachmann, New Canaan, CT (US)

(73) Assignee: Cambridge Medical Technologies LLC, Rockville, MD (US)

( * ) Notice: Subject to any disclaimer, the term of this patent is extended or adjusted under 35 U.S.C. 154(b) by 0 days.

(21) Appl. No.: 16/900,874

(22) Filed: Jun. 13, 2020

(65) Prior Publication Data
US 2021/0038127 A1 Feb. 11, 2021

Related U.S. Application Data

(60) Provisional application No. 62/884,286, filed on Aug. 8, 2019.

(51) Int. Cl.
*A61B 5/145* (2006.01)
*A61B 5/1491* (2006.01)
*A61B 5/1468* (2006.01)
*A61B 5/1486* (2006.01)

(52) U.S. Cl.
CPC .......... *A61B 5/1486* (2013.01); *A61B 5/1451* (2013.01); *A61B 5/1468* (2013.01);
(Continued)

(58) Field of Classification Search
CPC ...... A61B 5/145; A61B 5/1451–14514; A61B 5/14546; A61B 5/1468; A61B 5/1477;
(Continued)

(56) References Cited

U.S. PATENT DOCUMENTS 4,197,853 A 4/1980 Parker
4,526,176 A 7/1985 Bremer et al.
(Continued)

FOREIGN PATENT DOCUMENTS

EP 1 003 033 A1 5/2000
KR 10-2006-0082852 A 7/2006
(Continued)

OTHER PUBLICATIONS

Jitao Huang, Wei Huang, and Titi Wang, "Catalytic and Inhibitory Kinetic Behavior of Horseradish Peroxidase on the Electrode Surface," Sensors, 12, 14556-14569 (Year: 2012).*
(Continued)

*Primary Examiner* — Eric F Winakur
*Assistant Examiner* — Alice Ling Zou
(74) *Attorney, Agent, or Firm* — The Marbury Law Group, PLLC (57) ABSTRACT

Systems and methods are provided for determining levels of a target analyte in a biological sample. A transdermal sampling and analysis device may include a substrate, at least one disruptor mounted on the substrate, a reservoir configured to collect and contain a biological sample, at least two electrodes, and an electrochemical bioassay configured to determine levels of a target analyte in the biological sample. The at least one disruptor of the transdermal sampling and analysis device may be configured to generate a localized heat capable of altering permeability characteristics of a stratum corneum layer of skin of an organism.

18 Claims, 6 Drawing Sheets

(52) U.S. Cl.
CPC ........ *A61B 5/1491* (2013.01); *A61B 5/14514* (2013.01); *A61B 5/14546* (2013.01)

(58) Field of Classification Search
CPC ................ A61B 5/1486; A61B 5/1491; A61B 2018/00041; A61B 18/04; A61B 18/08; A61B 5/00; A61B 5/14507; A61B 5/1473–14735; A61B 5/4806; A61B 5/4842; A61B 5/6801; A61B 2562/125; A61B 5/14532; G01N 33/5308; G01N 33/53; G01N 33/68; G01N 33/6854; G01N 33/6869; G01N 33/74; G01N 33/566; G01N 27/26–27; G01N 27/327–3273; G01N 27/3275–3277; G01N 27/404; G01N 27/406; G01N 27/413; G01N 27/4145; G01N 33/48; G01N 33/50; G01N 33/5302; G01N 33/543–54306; G01N 33/54353–54373; G01N 33/5438; G01N 33/54393–544; G01N 33/548–549; G01N 33/557–559; G01N 33/58–581; G01N 33/6863; G01N 33/6881; G01N 2470/04–06; C12Q 1/001–005; C12Q 1/25; C12Q 1/28; C12Q 2525/205; C12Q 2521/525; C12Q 1/26; C12Q 1/42; C12Q 1/68; C12Q 1/6832–6837; C12Q 2500/00; C12Q 2520/00; C12Q 2565/50; C12Q 2565/607; C12N 11/04; C12N 11/098; C12N 11/10–12
See application file for complete search history.

(56) References Cited

U.S. PATENT DOCUMENTS

| | | | |
|---|---|---|---|
| 4,775,361 A | 10/1988 | Jacques et al. |
| 4,821,733 A | 4/1989 | Peck |
| 4,909,256 A | 3/1990 | Peck |
| 5,019,034 A | 5/1991 | Weaver et al. |
| 5,123,902 A | 6/1992 | Muller et al. |
| 5,149,629 A | 9/1992 | Rishpon et al. |
| 5,176,881 A | 1/1993 | Sepaniak et al. |
| 5,203,327 A | 4/1993 | Schoendorfer et al. |
| 5,284,748 A | 2/1994 | Mroczkowski et al. |
| 5,330,527 A | 2/1994 | Mroczkowski et al. |
| 5,362,307 A | 7/1994 | Montecalvo et al. |
| 5,366,454 A | 11/1994 | Currie et al. |
| 5,380,272 A | 1/1995 | Gross |
| 5,458,140 A | 10/1995 | Eppstein et al. |
| 5,711,861 A | 1/1998 | Ward et al. |
| 5,722,397 A | 3/1998 | Eppstein |
| 5,730,714 A | 3/1998 | Guy et al. |
| 5,885,211 A | 3/1999 | Eppstein et al. |
| 5,983,131 A | 11/1999 | Weaver et al. |
| 5,985,116 A | 11/1999 | Ikeda et al. |
| 6,022,316 A | 2/2000 | Eppstein et al. |
| 6,046,051 A | 4/2000 | Jina |
| 6,056,738 A | 5/2000 | Marchitto et al. |
| 6,124,597 A | 9/2000 | Shehada et al. |
| 6,144,869 A | 11/2000 | Berner et al. |
| 6,175,752 B1 | 1/2001 | Say et al. |
| 6,233,471 B1 | 5/2001 | Berner et al. |
| 6,270,651 B1 | 8/2001 | Essalik et al. |
| 6,281,006 B1* | 8/2001 | Heller ............... C12Q 1/002 204/403.09 |
| 6,342,037 B1 | 1/2002 | Roe et al. |
| 6,393,318 B1 | 5/2002 | Conn et al. |
| 6,436,078 B1 | 8/2002 | Svedman |
| 6,464,687 B1 | 10/2002 | Ishikawa et al. |
| 6,572,542 B1 | 6/2003 | Houben et al. |
| 6,597,946 B2 | 7/2003 | Avrahami et al. |
| 6,730,200 B1 | 5/2004 | Stewart et al. |
| 6,887,202 B2 | 5/2005 | Currie et al. |
| 6,922,586 B2 | 7/2005 | Davies |
| 7,001,495 B2 | 2/2006 | Thomas |
| 7,223,364 B1 | 5/2007 | Johnston et al. |
| 7,287,318 B2 | 10/2007 | Bhullar et al. |
| 7,826,981 B2 | 11/2010 | Goode, Jr. et al. |
| 8,173,380 B2 | 5/2012 | Yang et al. |
| 8,333,874 B2 | 12/2012 | Currie |
| 8,364,228 B2 | 1/2013 | Currie et al. |
| 9,877,673 B2 | 1/2018 | Currie et al. |
| 10,376,146 B2 | 8/2019 | Mujeeb-U-Rahman et al. |
| 2001/0052459 A1 | 12/2001 | Essalik et al. |
| 2002/0051975 A1 | 5/2002 | Li et al. |
| 2002/0055704 A1 | 5/2002 | Scott et al. |
| 2002/0169394 A1 | 11/2002 | Eppstein et al. |
| 2003/0003524 A1 | 1/2003 | Taniike et al. |
| 2003/0100040 A1 | 5/2003 | Bonnecaze et al. |
| 2003/0100846 A1 | 5/2003 | Custer et al. |
| 2003/0130616 A1 | 7/2003 | Steil et al. |
| 2003/0208152 A1 | 11/2003 | Avrahami et al. |
| 2003/0214304 A1 | 11/2003 | Karinka et al. |
| 2003/0225362 A1 | 12/2003 | Currie et al. |
| 2004/0039343 A1 | 2/2004 | Eppstein et al. |
| 2004/0058172 A1 | 3/2004 | Summers et al. |
| 2004/0157319 A1 | 8/2004 | Keen |
| 2004/0180391 A1 | 9/2004 | Gratzl et al. |
| 2004/0193219 A1 | 9/2004 | Asano et al. |
| 2004/0217018 A1 | 11/2004 | Leong et al. |
| 2004/0224369 A1 | 11/2004 | Cai et al. |
| 2004/0253304 A1 | 12/2004 | Gross et al. |
| 2005/0042766 A1 | 2/2005 | Ohman et al. |
| 2005/0045476 A1 | 3/2005 | Neel et al. |
| 2005/0069454 A1 | 3/2005 | Bell |
| 2005/0175505 A1 | 8/2005 | Cantor et al. |
| 2005/0182307 A1 | 8/2005 | Currie et al. |
| 2005/0226921 A1 | 10/2005 | Kortzebom |
| 2005/0228340 A1 | 10/2005 | Cleary et al. |
| 2006/0241514 A1 | 10/2006 | Davies |
| 2006/0285996 A1 | 12/2006 | Ohman et al. |
| 2009/0281404 A1 | 11/2009 | Currie et al. |
| 2009/0308742 A1 | 12/2009 | Paranjape |
| 2010/0160755 A1 | 6/2010 | Oviatt et al. |
| 2012/0073986 A1 | 3/2012 | Jackson et al. |
| 2012/0150004 A1 | 6/2012 | Currie et al. |
| 2012/0181189 A1 | 7/2012 | Merchant |
| 2012/0245445 A1 | 9/2012 | Black et al. |
| 2012/0283539 A1 | 11/2012 | Freeman et al. |
| 2013/0144142 A1 | 6/2013 | Vidalis et al. |
| 2014/0135679 A1 | 5/2014 | Mann et al. |
| 2014/0275895 A1 | 9/2014 | Vidalis et al. |
| 2015/0065818 A1 | 3/2015 | Say et al. |
| 2015/0140584 A1 | 5/2015 | Wilsey |
| 2016/0135721 A1* | 5/2016 | Bollmann .......... A61B 5/14546 600/310 |
| 2017/0325724 A1 | 11/2017 | Wang et al. |
| 2018/0338713 A1* | 11/2018 | Polsky ................ A61B 5/685 |
| 2019/0076075 A1* | 3/2019 | Miller ............... A61B 5/14539 |
| 2019/0216374 A1 | 7/2019 | Hoss et al. |

FOREIGN PATENT DOCUMENTS

| | | |
|---|---|---|
| WO | 97/19344 A1 | 5/1997 |
| WO | 99/56613 A1 | 11/1999 |
| WO | 2006/063063 A2 | 12/2005 |
| WO | 2006/050032 A2 | 5/2006 |
| WO | 2007/070093 A2 | 6/2007 |
| WO | 97/42882 A1 | 11/2007 |
| WO | 2009/042631 A2 | 4/2009 |
| WO | 2011/053715 A2 | 5/2011 |
| WO | WO-2014149514 A1 * | 9/2014 ......... A61B 5/14532 |

OTHER PUBLICATIONS

Xu, "Electrochemical detection optimized for capillary liquid chromatographic determination of neuroactive compounds", 2012, Doctoral Dissertation, University of Pittsburgh, Web, Retrieved from http://d-scholarship.pitt.edu/10478, 137 pages.

(56) References Cited

OTHER PUBLICATIONS

Xu, "Electrochemical Detection Optimized for Capillary Liquid Chromatographic Determination of Neuroactive Compounds", University of Pittsburgh, 137 pages, Nov. 10, 2011.
Boder, et al., "Development of Monoclonal Antibodies for an Assay of Cardiac Tropinin-I and Preliminary Results in Suspected Cases of Myocardial Infarction", Clin. Chem. 38/11, pp. 2203-2214, (1992).
Currie, et al., "Novel Non-Intrusive Trans-Dermal Remote Wireless Micro-Fluidic Monitoring System Applied to Continuous Glucose and Lactate Assays for Casualty Care and Combat Readiness Assessment", XP-002525792, RTO-MP-HFM-109, pp. 24-1 to 24-18, (Aug. 16-18, 2004).
De Almeida, et al., "Measurement of Melatonin in body fluids: Standards, protocols and procedures", Childs Nerv. System 27, DOI 10.1007/s00381-010-1278-8, pp. 879-891, (2011).
Linder, et al., "Heparin-Binding Protein: An Early Marker of Circulatory Failure in Sepsis", Department of Clinical Sciences, Division of Infection Medicine, Lund University, Lund, Sweden, CID 2009:49, 8 pages, (Oct. 1, 2009).
Matsuyama, et al., "Soluble interleukin-6 receptors in inflammatory bowel disease: relation to circulating interleukin-6", GUT 36, pp. 45-49; (1995).
Wei, et al., "A novel sandwich immunosensing method for measuring cardiac troponin 1 in sera", Analytical Biochemistry 321, pp. 209-216, (2003).
Yanez, et al., "Development and Validation of an Ultrasensitive Procalcitonin Sandwich Immunoassay", MDPI, High-Throughput, 6, 18; doi:10.3390/ht6040018, www.mdpi.com/journal/hightraughtput, 12 pages, (2017).
International Search Report and Written Opinion received from the Korean Intellectual Property Office in related International Application No. PCT/US2014/027362 dated Sep. 1, 2014.
International Search Report with Written Opinion cited in related Patent Application No. PCT/US2011/06558, 15 pages dated Jul. 25, 2012, (Jul. 27, 2012).
International Search Report and Written Opinion cited in related Patent Application No. PCT/US05/44287, 5 pages, (dated Aug. 28, 2006).
International Preliminary Examination Report cited in related Patent Application No. PCT/US01/17081, 5 pages, (dated Sep. 17, 2004).
Balabanova, et al., "Detection of Drugs in Sweat (Nachweis von Drogen im schweib)" Beitr. Gerichtl. Med., vol. 48, pp. 45-49, (1990).
Henderson et al., "Excretion of Methadone and Metabolites in Human Sweat," Research Communications in Chemical Pathology and pharmacology, vol. 5, No. 1, pp. 1-8, (Jan. 1973).
Peck et al., "Outward Transcutaneous Chemical Migration: Impliations for Diagnostics and Dosimetry", Skin Pharmacol, vol. 1, No. I, pp. 14-23, (1988).
Phillips et al., "A Sweat-Patch Test for Alcohol Consumption: Evaluation in Continuous and Episodic Drinkers", Alcohol: clinical and Experimental research, vol. 4, No. 4, pp. 391-395, (1980).
"SpectRx An Innovactive Medical Technology Company" [online], Copyright 2004, 1 p., Retrieved from the Internet hhtp://www.spectrx.com. (Aug. 31, 2004).
Schneider et al., "B-Fit System: Bio-Flips Integrable Transdermal Microsystem", ARO Workshop on Biomolecular Signaling, Energy Transfer, and Transduction Processes, Cashiers, NC, 16 pages, (May 14-17, 2000).
Smith et al., "Cocaine in Hair, Saliva, Skin Swabs, and Urine of Cocaine Users' Children", Forensic Science International, vol. 83, pp. 179-189, (1996).
European Search Report dated Apr. 29, 2009, issued in US Application No. PCT/US2006023194, (May 13, 2009).
Nijdam, A.J., et al., "Fluidic encapsulation in SU-8 [micro]-reservoirs with [micro]-fluidic through-chip channels", Sensors and Actuators A, vol. 120, p. 172-183; (Apr. 29, 2005).
Gadre et al., "Fabrication of a fluid encapsulated dermal patch using multilayered SU-8," Sensors And Actuators A: Physical, 114(2-3):478-485 (2004).
Paranjape et al., "A PDMS dermal patch for non-intrusive transdermal glucose sensing," Sensors and Actuators A : Physical, 104(3):195-204 (2003).
Heller, et al., Electrochemical Glucose Sensors and their Applications in Diabetes Management, Chem Review, Department of Chemical Engineering, Univ, of Texas, (Sep. 17, 2007).
Merchant, et al., High-Sensitivity Amperometric Biosensors Based on Ferrocene-Modified Linear Poly (ethylenimine), Langmuir Article, 2009 American Chemical Society, (Mar. 24, 2009).
Merchant, et al., "Effect of Mediator Spacing on Electrochemical and Enzymatic Response of Ferrocene Redox Polymers", J. Phys. Chem. 114, p. 11627-11634, (2010).
Xu, et al., Construction of phospholipid anti-biofouling multilayer on biomedical PET surfaces, Applied Surface Science 255, pp. 538-540, (2008).
Carneiro-Da-Cunha, et al., Physical and thermal properties of a chitosan/alginate nanolayered PET film, Carbohydrate Polymers 82, pp. 153-159, (2010).
International Search Report and Written Opinion cited in related Patent Application No. PCT/US2012/067265 dated Mar. 28, 2013.
International Preliminary Report on Patentability received in related Patent Application No. PCT/US2011/063558 dated Jun. 20, 2013.
International Preliminary Report on Patentability received in related Patent Application No. PCT/US2012/067265 dated Jun. 12, 2014.
International Search Report and the Written Opinion from the International Searching Authority in related Application No. PCT/US2020/065384 dated Apr. 19, 2021.

\* cited by examiner

NON-INVASIVE TRANSDERMAL SAMPLING AND ANALYSIS DEVICE INCORPORATING AN ELECTROCHEMICAL BIOASSAY

RELATED APPLICATIONS

This application claims priority to U.S. Provisional Patent Application No. 62/884,286 entitled "Non-Invasive Transdermal Sampling and Analysis Device Incorporating an Electrochemical Bioassay" filed on Aug. 8, 2019, the entire contents of which are hereby incorporated by reference for all purposes.

BACKGROUND

A biosensor is a device which measures the presence or amount of an analyte in a biological sample. A biosensor may include three main parts: i) biologically reactive elements sometimes referred to as reagents. Reagents may include biological materials (e.g., tissues, microorganisms, organelles, cell receptors, enzyme, antibodies, and take acid, etc.), a biologically derived material or biomimic, wherein the reagent may be created by biological engineering; ii) a transducer or detector element which may work in a physiochemical way (e.g., optical, piezoelectric, electrochemical, etc.) to transform the signal resulting from the interaction of the analyte being measured with the reagent into another signal that can be more easily measured and quantified; and iii) associated electronics or signal processors that are primarily responsible for the display of the results.

Enzymatic biosensors involve placement of an enzyme in close proximity to an electrode surface. The enzyme involved must catalyze a reaction between the analyte and reagent, which involves consuming of electroactive reactant or generation of electroactive species. The depletion or production process is then monitored. The monitored value of the depletion or production process may provide a direct measurement of the analyte concentration.

Certain small molecule analytes of interest may not be involved in enzymatic reactions. Rather, certain small molecule analytes may instead selectively bind to specific antibodies, aptamers, or affimers that may be linked to enzymes, such as those used in conventional enzyme-linked immunosorbent assays (ELISAs). An ELISA is a plate-based assay technique designed for detecting and quantifying substances such as peptides, proteins, antibodies and hormones. Specifically, in an ELISA, the substance of interest (i.e., target analyte, antigen, or biomolecule of interest) may be immobilized on a solid surface and then complexed with an antibody that is linked to an enzyme. In such assays, the antigen may be generally detected by assessing the conjugated enzyme activity via incubation with a substrate to produce a measurable product. In particular, the antigen may be typically immobilized through binding to a capture (primary) antibody that is chemically bound to a solid surface electrode.

While effective for antigen detection, conventional ELISA techniques must be performed through a series soak and wash steps where each component is introduced separately. Since such steps involve complicated bench-top methods that may take hours or days to complete, conventional ELISA detection is generally incompatible with real-time sampling and analysis.

SUMMARY OF THE INVENTION

Embodiment transdermal sampling and analysis devices may include a substrate, at least one disruptor mounted on the substrate in which the at least one disruptor is configured to generate a localized heat capable of altering permeability characteristics of a stratum corneum layer of skin of an organism, a reservoir configured to collect and contain a biological sample, at least two electrodes, and an electrochemical bioassay configured to determine levels of a target analyte in the biological sample. In some embodiment transdermal sampling and analysis devices, the at least one disruptor of the transdermal sampling and analysis device may be configured to generate a localized heat capable of altering permeability characteristics of a stratum corneum layer of skin of an organism.

In some embodiment transdermal sampling and analysis devices, the target analyte may be selected from cardiac troponin I (cTnI), melatonin, procalcitonin (PCT), heparin-binding protein (HBP), or interleukin-6 (IL-6).

In some embodiment transdermal sampling and analysis devices, the electrochemical bioassay may include a first small molecule binding element bound to a surface of at least one of the electrodes, at least one barrier layer covering a remainder of the surface, and a second small molecule binding element linked to an enzyme. In some embodiment transdermal sampling and analysis devices, the second small molecule binding element, the linked enzyme, and at least one substrate of the linked enzyme may be suspended in a hydrogel on top of the at least one of the electrodes.

In some embodiment transdermal sampling and analysis devices, the target analyte may be a small molecule that includes at least one binding site for each of the first small molecule binding element and the second small molecule binding element. In some embodiment transdermal sampling and analysis devices, the linked enzyme may catalyze a reaction of the at least one substrate. In some embodiment transdermal sampling and analysis devices, the reaction may cause transfer of electrons to the at least one of the electrodes when carried out in proximity to the first small molecule binding element.

In some embodiment transdermal sampling and analysis devices, the first and second small molecule binding elements may be selected from antibodies, aptamers, or affimers. In some embodiment transdermal sampling and analysis devices, the linked enzyme may be selected from alkaline phosphatase (ALP) or horseradish peroxidase (HRP), and the substrate of the linked enzyme may be selected from phenyl phosphate and hydrogen peroxide.

In some embodiment transdermal sampling and analysis devices, the electrochemical bioassay may further include an electron mediator suspended in the hydrogel. In some embodiment transdermal sampling and analysis devices, the electron mediator may be selected from ferrocene, osmium bipyridine complexes, ruthenium phthalocyanine complexes, a quinone, a tetrathialfulvalene (TTF), a tetracyanoquinodimethane (TCNQ), or a thionine.

BRIEF DESCRIPTION OF THE DRAWINGS

The accompanying drawings, which are incorporated herein and constitute part of this specification, illustrate exemplary aspects of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

The words "exemplary" and/or "example" are used herein to mean "serving as an example, instance, or illustration." Any embodiment described herein as "exemplary" and/or "example" is not necessarily to be construed as preferred or advantageous over other embodiments.

The term "in situ" is used herein to refer to tests and/or measurements performed using a natural composition/tissue in an environment that is at least partially subject to artificial control. For example, a novel transdermal biosensor may be said to be operating in situ when it is placed on the surface of a patient's skin while it disrupts the stratum corneum continuously to generate a biological fluid sample and analyze the generated biological fluid sample while the biosensor remains in place on the surface of the patient's skin.

The terms "analyte," "analyte of interest," "antigen," "target analyte," and "small molecule" are used interchangeably herein to refer to a substance that is detectable in a biological sample, such as blood or interstitial fluid.

Biosensors combine a biological sample with a physiochemical detector component (i.e., reagent) to allow for the detection of an analyte (that is, a substance or chemical constituent that is determined in an analytical procedure). The signal, generated as a result of interaction between the detector (i.e., reagent) and the analyte contained within the biological sample, may be electrical, optical, thermal, etc., is transformed by the means of suitable transducer element into a measurable parameter such as current or voltage. The biosensor selectivity against the target analyte may be determined by the physiochemical detector, while sensitivity may be dependent on the transducer.

Compared to other detection methods, such as colorimetric methods, chemiluminescence, fluorometric methods, high performance liquid chromatography (HPLC), and magnetic resonance spectroscopy, amperometric biosensors have exhibited advantages such as simplicity, portability, rapid response, high specificity, and simple operation. The response current in amperometric biosensors may be continuously monitored, and may be associated with oxidation and/or reduction of an electroactive species involved in the recognition process and relates (ideally directly) to the target analyte concentration. Specifically, the response current may result from such oxidation or reduction at inert electrodes, with the reactions driven by a constant applied potential.

Amperometry may be performed using a two or three electrode electrochemical cell, with a working electrode, a reference electrode, and a counter electrode. Typically, an electrical current is measured between the working and counter electrodes, at a constant potential, applied between the working and reference electrodes. Amperometric sensing may be used in enzyme-based sensors, where the enzyme catalyzes a redox reaction between the detector (i.e., reagent) and the analyte contained within the biological sample. The redox reaction either generates electrons that reduce the working electrode, or results in oxidized reaction product that is in turn reduced, directly or indirectly, by the working electrode. These generated electrons may increase the measured electrical current and thus, may be proportional to or indicate the amount or concentration of analyte in the biological sample.

The reference electrode may provide a fixed potential against which the potential applied to the working electrode is measured and controlled. The electrical current generated between the working electrode and the counter electrode may be measured when the potential between them is maintained at a constant level. This constant level may be used to drive the reaction at the working electrode, and may be maintained using a potentiostat.

In instances where a positive potential, relative to the reference electrode, is used to drive the reaction at the working electrode, an oxidation reaction occurs and the working electrode monitors the oxidation of a species near the surface. For example, electrons from an enzyme-catalyzed redox reaction may be transferred to the working electrode, and the measured current flow (i.e., oxidation current) resulting from the transfer of electrons may indicate the relative concentration of the analyte. In instances where a negative potential is used to drive the reaction, a reduction reaction occurs and the working electrode monitors the reduction of a species near the surface. That is, a product of the enzyme-catalyzed redox reaction may be reduced by accepting electron(s) at the working electrode, and the measured current flow results from the transfer of electrons (i.e., reduction current) may indicate the relative concentration of the analyte. Such biosensors are typically based on enzymes that either consume oxygen, generate hydrogen peroxide, or indirectly produce a reduced form of a cofactor (e.g., NADH, NADPH, $FADH_2$, coenzymeQ, etc.) with the catalytic breakdown of a substrate.

Biosensors designed for patient home monitoring may use a blood droplet collected from a patient's finger, arm, or other location on the body as the sample for analysis. Such conventional biosensors designed for patient home monitoring suffer from a number of disadvantages. For example, biosensors that use blood as a biological sample are typically painful and inconvenient to obtain the biological sample. In addition to being painful, such conventional biosensors are also designed in a manner so as to require a relatively large blood sample to accurately determine analyte concentration.

Another disadvantage of the conventional biosensors is that they require several steps in order to analyze the biological sample. Conventional biosensors require loading a test strip into an analyzer collecting the biological samples (e.g., blood), into the test strip, and disposal of the test strip. This multi-step process is time consuming and may cause contamination or loss of the biological sample during the collection and/or delivery.

Therefore, a one-step biosensor may provide effective in situ measurement of analyte concentrations from small quantities of the interstitial fluid collected from the capillary-like channels of the patient's skin. Such systems (referred to herein as the "transdermal sampling and analysis device" or "transdermal biosensor") are described in U.S. Pat. No. 9,877,673, entitled "Transdermal Sampling and Analysis Device," and U.S. patent application Ser. No. 14/208,344, entitled "Methods of Manufacture to Optimize Performance of Transdermal Sampling and Analysis Device," the contents of which are hereby incorporated by reference for the purpose of describing the systems and methods disclosed therein.

The transdermal biosensor may also enable the entire process of analyzing a biological sample including disrupting the skin cells, collecting biological samples, reacting the biological sample with a biologically reactive element, and sensing the signals generated by the reaction, to be performed in a single device. In contrast, in in vitro measurements, such as those performed using conventional blood tests or withdrawal techniques, a biological sample (e.g., interstitial fluid) may be collected, and subsequently tested for an analyte (or other measurable property) by submitting it to a remote assay or sensor. By incorporating a sampling device and analyzing device in a singular in situ test, a smaller biological sample may be obtained and the potential for contamination of the biological sample may be dramatically reduced. The time required to obtain a sample and perform an analysis of the sample may be also reduced.

In transdermal analysis and sensing devices/biosensors, a patient's stratum corneum may be disrupted through the application of localized heat to allow interstitial fluid to permeate from capillary-like channels in the stratum corneum and may be collected. In some embodiments, the concentration of an analyte may be quantified by the reaction of the biological sample with a biologically reactive element. However, such techniques may not be suitable for quantifying certain small molecule analytes of interest.

In clinical application fields, enzyme-based immunoassays that are based on selective antigen-antibody binding are a widely used conventional detection principle. In this analysis method, the antigen (i.e., analyte of interest) or antibody may be labeled by an enzyme, and the activity of such enzyme may be measured based on the molecular interaction between the antigen and antibody. In electrochemical assays, for example, the enzymatic activity may be measured based on a current signal generated at an electrode. Such electrical currents may be detected using amperometric detection. Electrochemical assays offer an alternative to spectrophotometry and fluorescence detection of analytes in biological samples, as they command a relatively low cost and have adequate sensitivity for point-of-care testing or field detection. While immunoassays may provide a higher degree of accuracy or sensitivity, immunoassays that employ electrochemical detection typically still require laboratory equipment and instrumentation.

A transdermal sampling and analysis device according to, the various embodiments disclosed herein may be capable of measuring a small molecule analyte by incorporating an electrochemical bioassay. The bioassay may be utilized in the embodiment device to detect the level or concentration of the target analyte in a biological sample based on a generated electrical current.

The electrochemical bioassays of various embodiments disclosed herein may apply the steps and elements of a conventional enzyme-linked immunosorbent assay (ELISA) or enzyme immunoassay (EIA) into one step within a transdermal sampling and analysis device. A small molecule binding element (i.e., a capture antibody) may be bound to the surface of an electrode along with an electrode-barrier agent. A hydrogel that incorporates both an enzyme-linked small molecule binding entity (i.e., a detection antibody) as well as its corresponding substrate may be overlayed onto the electrode. In this manner, a "sandwich"-assay type detection of the target analyte may be performed in real-time.

Using an embodiment transdermal sampling and analysis device, a disruptor unit may provide a localized heat to the stratum corneum of a patient. The localized heat may render the cells of the stratum corneum permeable to interstitial fluid, thus allowing interstitial fluid (i.e., biological sample) to be collected. An amount of analyte present in collected biological sample may be quantified based on the electrical current generated as a result of the enzyme-catalyzed reaction of the substrate close to the electrode surface. Once the disruptor unit of the embodiment transdermal sampling and analysis device is removed from the skin, stratum corneum cells become impermeable again by returning to their original formation and closing the capillary-like channels.

A transdermal sampling and analysis device according to various embodiments may be used in methods for detecting a target analyte in a biological sample. For example, such method may include providing a localized heat capable of altering permeability characteristics of a stratum corneum layer of a patient's skin, with the localized heat being generated by at least one disruptor mounted on a substrate of the transdermal sampling and analysis device. The method may also include collecting and containing a biological sample within a reservoir of the transdermal sampling and analysis device, and determining levels of the target analyte in the biological sample using an electrochemical bioassay.

Figure 1A:
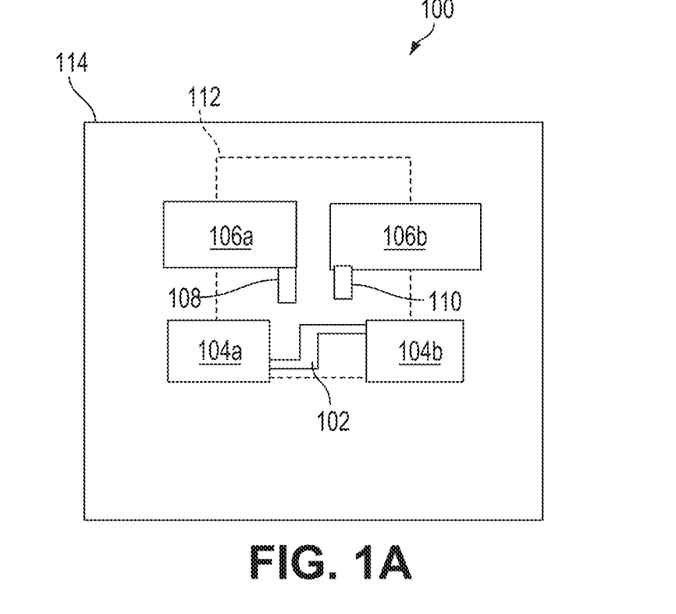
FIG. 1A is a component diagram of a transdermal sampling and analysis device suitable for use with various embodiments.

FIG. 1A is a block diagram illustrating the functional components of an example transdermal sampling and analysis device 100. A transdermal sampling and analysis device 100 may include a disruptor 102 connected to the positive and negative electrical poles of a signal generator 104a, 104b. In an embodiment, the disruptor 102 may function as a resistive element. The disruptor 102 produces heat as electrical current is applied through the disruptor 102. When placed on the skin, the localized heat generated by the disruptor 102 may cause disruption to the skin cells facilitating the flow of interstitial fluid onto the surface of the transdermal sampling and analysis device 100. The disruptor 102 may be made from a variety of materials which exhibit the appropriate heating and control properties to provide the precise heating control properties required to disrupt the skin cells without damaging them. After a brief period of increased permeability due to the application of localized heat, the cells return to their normal function.

The materials used to create the disruptor 102 may be selected for relative ease of manufacture as well as cost considerations. Materials such as titanium, tungsten, stainless steel, platinum and gold may be preferably used to form the disruptor 102. In a preferred embodiment, gold may be used to form the disruptor 102.

In an embodiment, when analyzing concentrations of a target analyte in an obtained biological sample, enzymatic reactions involving the analyte or another substrate may yield electrons that may be captured to generate anodic current between the sensing electrodes 108, 110, also referred to as counter electrode 108 and working electrode 110. Alternatively, the enzymatic reaction may consume electrons and generate cathodic current between the counter electrode 108 and the working electrode 110. The magnitude of the electrical current generated as a result of the chemical reaction may be proportional to the amount or concentration of the analyte contained in the obtained biological sample. In an embodiment, a voltage potential may be applied to the counter and working electrodes 108, 110 using a power generator (not shown). In this embodiment, the working electrode 110 may function as an anode and the counter electrode 108 may function as a cathode or vice versa. The magnitude of the measured electrical current may depend on the amount or concentration of analyte that is contained within the biological sample and the presence and selectivity of the enzyme and any required cofactor. An ammeter may be used to measure the electrical current generated.

An embodiment transdermal sampling and analysis device 100 may further include a reservoir 112 for collecting and containing biological samples such as interstitial fluids that flow from capillary-like channels in disrupted stratum corneum. The reservoir 112 may be formed under the disruptor 102 and sensing electrodes 108, 110. When the transdermal sampling and analysis device 100 is placed on the subject's skin with the disruptor 102 contacting the skin, the reservoir 112 may effectively be positioned above the disruptor 102 and electrodes 108, 110 to contain the released interstitial fluid biological sample. The reservoir 112 may also include a cover or lid to more effectively contain the fluid. A reservoir 112 may be created using conventional methods known in the art, for example, by the buildup of material by additive process or by subtractive process such as photolithography. A substrate 114 may form the support on which transdermal sampling and analysis device 100 components may be positioned or attached. The obtained biological sample may be analyzed without removing the device from the patient (i.e., an in situ process).

Figure 1B:
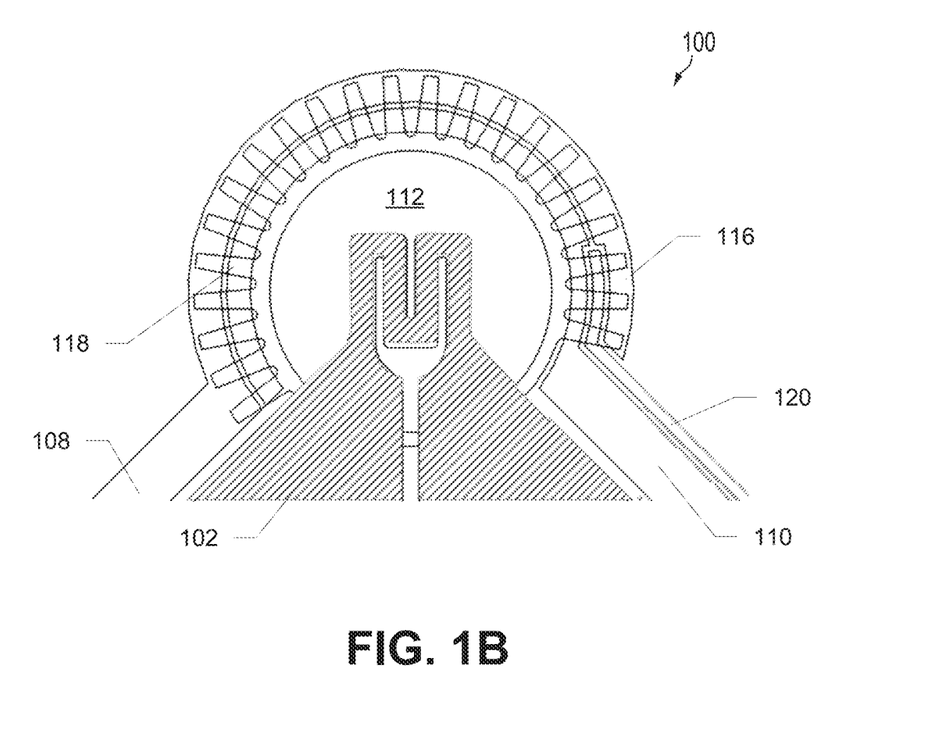
FIG. 1B is a top view of an embodiment transdermal sampling and analysis device suitable for use with various embodiments.

FIG. 1B illustrates an alternative embodiment of the transdermal sampling and analysis device 100. The device 100 may include a disruptor 102 having a serpentine configuration, within a collection reservoir 112. Leads capable of coupling the disruptor 102 to a voltage/current source may be extended to the corners of the transdermal sampling and analysis device 100. The disruptor 102 may be also positioned within a hole in a lid layer so that the disruptor 102 may be exposed to and may directly contact the subject's skin for disruption of the stratum corneum and the production of a biological fluid sample. A sensing chamber 116 may form a circular shape around the periphery of the collection reservoir 112. The sensing chamber 116 may contain sensing channels 118 in a radial arrangement. The circular sensing channels 118 may guide the flow of a biological sample through the circular-shaped sensing chamber 116. The sensing chamber 116 may provide the biological fluid sample over counter and working electrodes 108, 110. A reference electrode 120 may optionally be included. A biological fluid sample may be directed over the entire surface of counter and working electrodes 108, 110. The disruptor 102, counter and working electrodes 108, and optional reference electrode 120 may be all formed on a substrate layer.

As described, many different analysis techniques may be incorporated into the transdermal sampling and analysis device 100 to determine the amount or concentration of various analytes in a biological sample. For example, in addition to amperometric analysis techniques, such analysis may include coulometric, or potentiometric analysis techniques as additional or alternative methods that may be incorporated into the transdermal sampling and analysis device to determine levels/concentrations of analytes in a biological sample. In addition, electrochemical impedance analysis techniques may be incorporated to detect the presence of particular antibodies in a biological sample.

The counter and working electrodes 108, 110 may be made from any of a variety of materials which exhibit satisfactory conductivity characteristics and appropriate to the specific measurement used. In addition, the materials used to create the electrodes may be selected for relative ease of manufacture as well as cost considerations. Examples of materials exhibiting satisfactory conductivity characteristics for use as the counter and working electrodes 108, 110 may include gold, platinum, silver, carbon or other materials.

Selection of a substrate 114 for the transdermal sampling and analysis device 100 may depend on the coefficient of thermal expansion and conductivity of the material used to make the disruptor 102 of the transdermal sampling and analysis device 100. For example, the substrate 114 may be made of a material which has a coefficient of thermal expansion (CTE) that deviates from the CTE of the material used in the disruptor 102 by less than 50%, and preferably by less than 10%. In a further embodiment, the substrate 114 may be made of a material which has a coefficient of thermal conductivity (CTC) that is lower than 0.5 W/(m·K).

Biologically reactive elements, such as small molecule binding elements may be incorporated in the sensing chamber on the first side of the substrate 114. Such small molecule binding elements may include, for example, at least one capture (i.e., primary) antibody that is bound to the surface of at least one electrode (e.g., working electrode 110), and that contains a site to which a target analyte has a binding affinity. Further, the small molecule binding elements may include at least one detection (i.e., secondary) antibody that is linked to an enzyme, and that also includes at least one binding site for the target analyte. In various embodiments, the target analyte may be a small molecule that includes a first region (i.e., epitope) configured to bind to the capture antibody, and a second different region (i.e., epitope) that is configured to bind to the detection antibody.

In addition to antibodies, other small molecule binding elements may be used as biologically reactive elements, such as aptamers—that is, oligonucleotide or peptide molecules that bind to a specific target molecule. At the molecular level, aptamers may bind to a target site through non-covalent interactions. Aptamers may be useful in biotechnological and therapeutic applications as they offer the same high level of molecular recognition as antibodies, but may be engineered entirely in a test tube and may be readily produced by chemical synthesis. Other small molecule binding elements that may be used include affimers, which are proteins engineered to display peptide loops which provide a high affinity binding surface for a specific target protein.

The biologically reactive elements may also include at least one enzyme substrate, and optionally at least one electron mediator. The particular substrate and/or electron mediator used may be selected based on the enzyme utilized in the biologically reactive elements.

In various embodiments, the biologically reactive elements may be applied to the working electrode 110, the counter electrode 108 or both. As the stratum corneum is disrupted by disruptor 102, interstitial fluid may be released and begins to flow through the stratum corneum into the reservoir 112 by capillary action of the structure. The interstitial fluid may be directed to flow into the reservoir 112 and specifically over the surface of the counter and working electrodes 108, 110. The obtained interstitial fluid may come into contact with the biologically reactive elements on the surface of the counter and working electrodes 108, 110 causing a reaction that releases or consumes electrons. The counter and working electrodes 108, 110 may form anode and cathode of an electrolytic cell, enabling current flow through a device which can measure the current at a controllable potential.

An embodiment transdermal sampling and analysis device may be designed to deliver heat to the subject's skin through the disruptor 102 with a power density of 1-10 W per $mm^2$. In a preferred embodiment the disruptor 102 delivers heat to the subject's skin with a power density of 2-5 W per $mm^2$. The embodiment transdermal sampling and analysis devices may be made using a variety of different disruptor 102 configurations. The size and shape of the disruptor 102 may affect its resistive characteristics and consequently, its ability to generate a localized heat. In addition, the material selected to form the disruptor 102 may also affect its resistive characteristics and consequently, its ability to generate a localized heat. As with electrode material selection, disruptor materials may be selected from a wide variety of materials exhibiting satisfactory electrical conductance/resistive properties such that sufficient heat may be generated when specific voltages are applied to the disruptor leads. In addition, thermal conduction and resistance characteristics should be observed in an optimal disruptor material. Finally, ease of manufacturing processing and cost may determine the final selection of disruptor material. For example, a disruptor may be made of nichrome, titanium, tungsten, or gold. In a preferred embodiment, the disruptor 102 may be made from gold.

Figure 2:
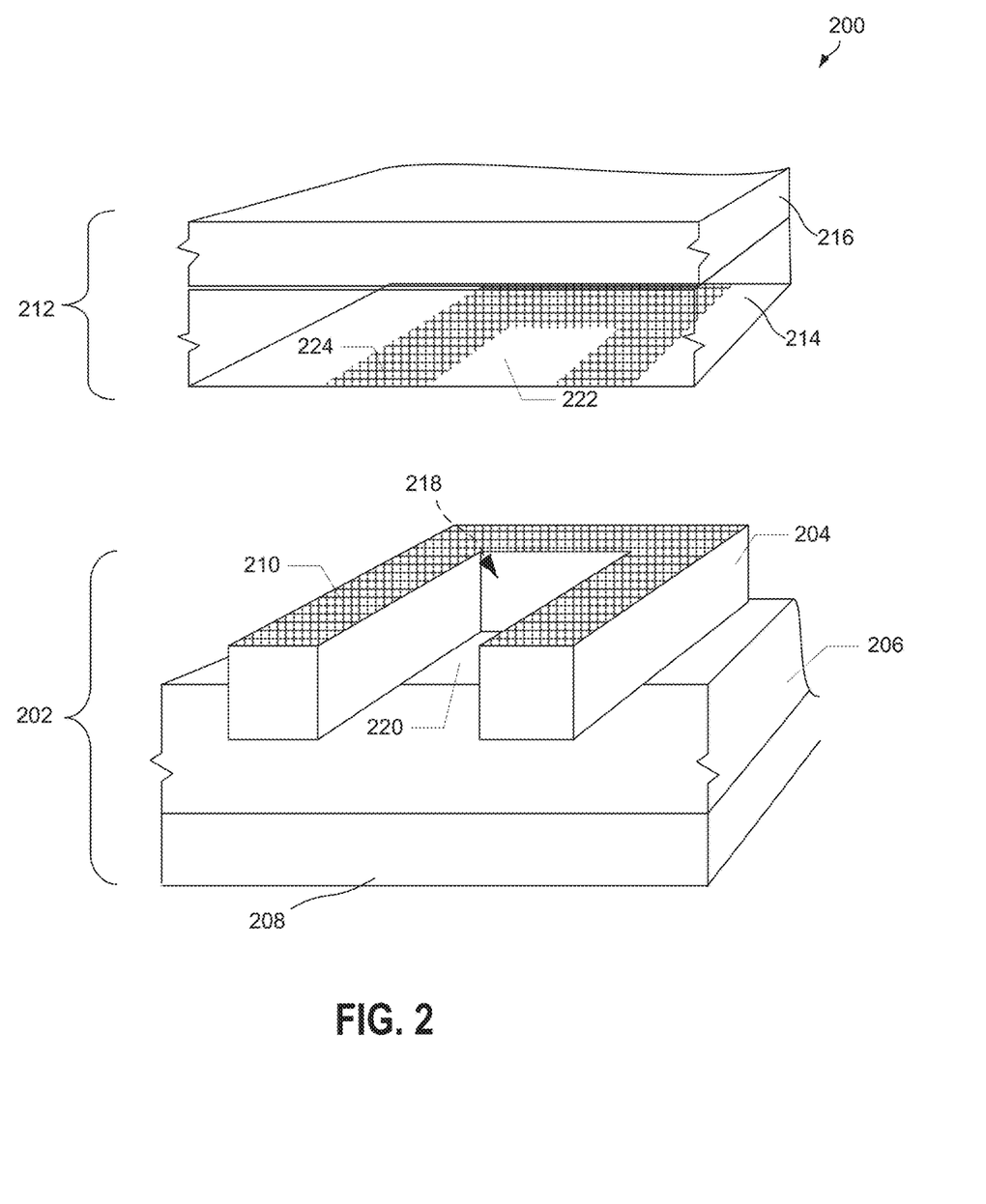
FIG. 2 is a perspective view of a portion of the lid and base structure of an embodiment transdermal sampling and analysis device suitable for use with various embodiments.

FIG. 2 illustrates a transdermal sampling and analysis device 200 according to an alternative embodiment. With reference to FIGS. 1A-2, the device 200 (not drawn to scale) may be formed using techniques similar to those discussed above. Representative components of the device 200 may include a base structure 202 that includes a spacer layer of channel support structures 204 formed over a counter electrode 206, which are formed over a base substrate 208. An adhesive (not shown) may be applied to the top surface 210 of the channel support structures 204. A lid structure 212 of the device 200 may have a working electrode 214 patterned onto a lid substrate 216. The base structure and lid structure shown in device 200 illustrate representative cross-section segments of a larger, three dimensional device 2600, and are not meant to limit the device 2600 based on size or shape. Further, while the base structure 202 is shown with two spacer layer channel support structures 204, they are representative of any of a plurality of sets of channel support structures that may be formed across a larger base structure.

As the lid structure 212 is brought down into position over the channel support structures 204, the adhesive on the channel support structures 204 may secure the lid structure 212 by contacting the working electrode 214. In this manner, channels 218 may be formed between exposed areas 220 of the counter electrode 206 and exposed areas 222 of the working electrode 214. Such exposed areas on both electrodes are defined around the direct contact between the top surface 210 of the spacer layer channel support structures 204 and a corresponding contact area 224 on the surface of the working electrode 214.

In an alternative embodiment, an additional spacer layer may be applied atop the channel forming spacer layer (i.e., channel support structures). In the various embodiments, the second spacer layer may be recessed back from the channel support structures in order to provide lift space between the channel support structures and a substantial portion of the working electrode surface.

While not limited to particular dimensions, in some embodiments the second spacer layer may be approximately the same thickness as the channel forming spacer layer. In an embodiment, the total thickness of the channel forming spacer layer and second spacer layer may be approximately the same as that of the single channel forming spacer layer, such as that of channel support structures 204. In this manner, the depth of the sensing channels (i.e., vertical space between the counter and working electrodes) may remain the same to avoid requiring a greater amount of fluid to fill.

Figure 3:
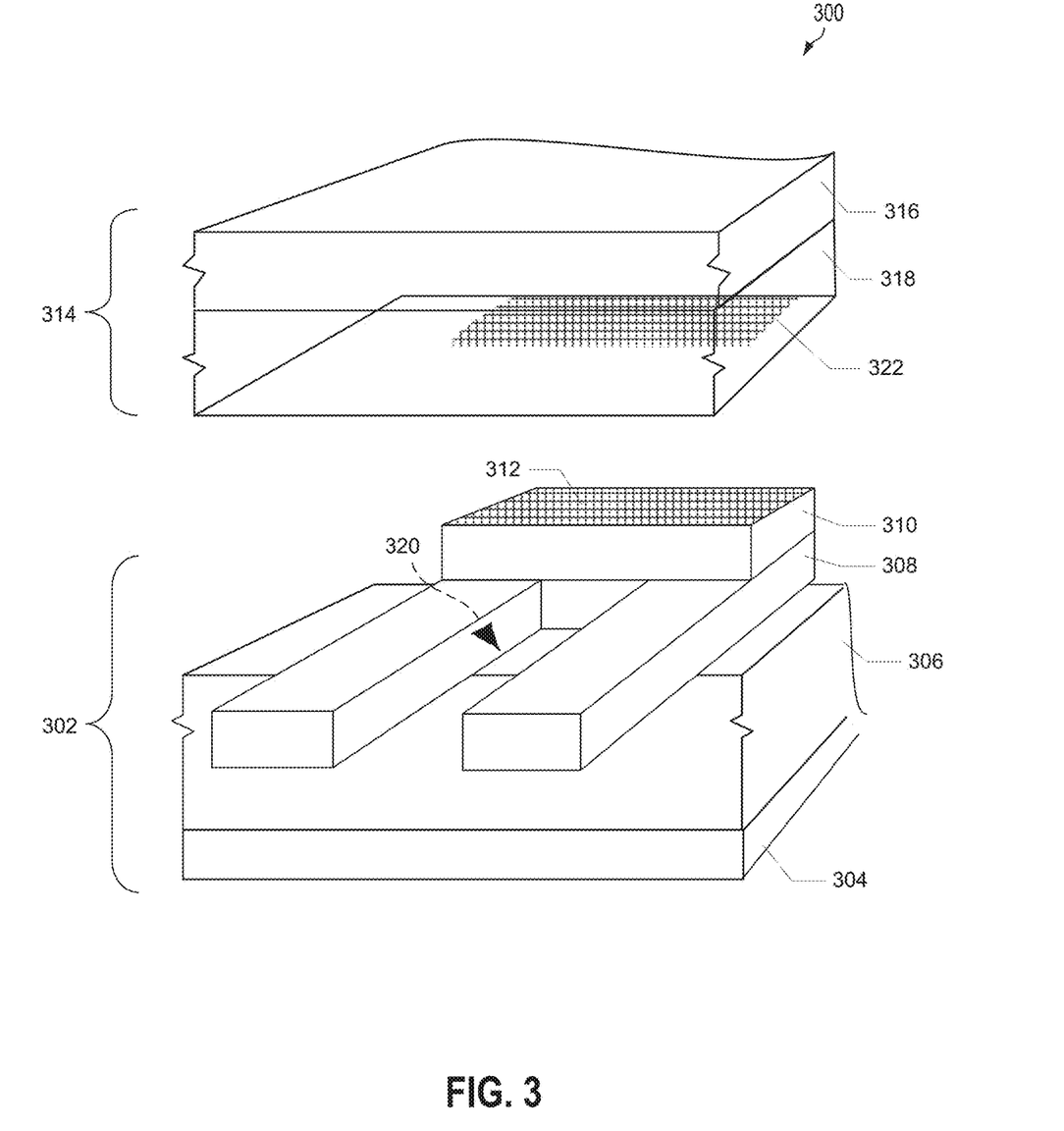
FIG. 3 illustrates a perspective view of a portion of the lid and base structure of an embodiment transdermal sampling and analysis device suitable for use with various embodiments.

FIG. 3 illustrates a transdermal sampling and analysis device 300 according to an alternative embodiment. With reference to FIGS. 1A-3, a base structure 302 may include a first conductive material layer applied to a base substrate 304, and patterned to form components including at least a counter electrode 306. Device 300 may also have a photoresist material applied over the counter electrode 306, which may be patterned to form channel support structures 308 in a channel forming spacer layer.

A second spacer layer material may be applied over the channel forming spacer layer to form a recessed second spacer layer 310. The degree to which the second spacer layer 310 is recessed back from the edge of the channel support structures 308 in the channel forming spacer layer may be variable according to different embodiments. Also depending on the type of material used to create the second spacer layer 310, an adhesive material may be selectively applied to the top surface 312 of the second spacer layer 310. For example, the second spacer layer material may be a double sided adhesive, thereby making an additional adhesive layer unnecessary. In various embodiments, the second spacer layer 310 as well as the channel forming spacer layer may each be around 10-20 µm thick.

A lid structure 314 of the device 300 may include a lid substrate 316 to which a second conductive material layer may be applied. The second conductive material layer may be patterned to form a working electrode 318, and various biologically reactive elements (e.g., capture antibodies, detection antibodies, enzymes, substrates, and an electrode barrier layer) may be applied to the surface of the working electrode 318 to create an electrochemical bioassay. As shown by the base structure 302 of device 300, channels 320 may be formed between exposed areas of the counter electrode 306 and exposed areas of the working electrode 318.

While the exposed areas on the counter electrode 306 are still defined by channel support structures 308, similar to device 200 in FIG. 2, such channel support structures 308 do not limit the exposed areas of the working electrode 318. Rather, the recessed second spacer layer 310 serves to raise the working electrode 318 off of the channel support structures 308, thereby providing a larger exposed area on the working electrode. That is, the only direct contact to the working electrode 318 of device 300 is by the top surface 312 of the recessed spacer layer 310. As a result, device 300 may have a smaller corresponding contact area 322 on the working electrode 318 in comparison to the contact area 224 of device 200. The larger exposed areas of the working electrode may provide a stronger signal and/or allow for use of a smaller working electrode to produce the same level of result.

In various embodiments, an electrochemical bioassay incorporated in a transdermal sampling and analysis device may enable real-time sensing of an analyte of interest from the biological sample. Such bioassay may be an immunoassay that uses that uses primary (i.e., capture) antibodies and enzyme-linked secondary (i.e., detection) antibodies as the small molecule binders. Specifically, a capture antibody may be bound to the surface of an electrode, such as the working electrode of a transdermal sensing and analysis device as described above.

In the sensing chamber 116 of the device 100, an electrode barrier layer may be plated onto the electrode 108, 110 surface to prevent unwanted electron transfer apart from the bound capture antibodies. In various embodiments, the electrode barrier layer may be a self-assembled monolayer of a non-reactive protein (e.g., bovine serum albumin (BSA)). The non-reactive protein may be applied using processes that include, but are not limited to, chemical and physical deposition processes.

In this manner, the entire surface of the electrode surface is either occupied by a bound capture antibody or covered by the barrier layer. The sensing chamber 116 may include a hydrogel directly above the electrode 108, 110, in which an enzyme-linked detection antibody and a substrate for the enzyme, may be suspended. The combination of the working electrode 110, the components applied to the surface of the working electrode, the hydrogel, and the components embedded in the hydrogel within in the sensing chamber 116 may be collectively referred to herein as a "sensing element." In various embodiments, all components of the sensing element are either bound to the electrode or suspended in hydrogel. Therefore, the electrochemical bioassay may create a one-step platform for small molecule sensing that is easily adaptable for various target analytes, and that enables real-time point-of-care analysis.

During use of the transdermal sensing and analysis device, a channel or chamber 116 that houses the sensing element (e.g., the sensing chamber) may fill with interstitial fluid from a reservoir/collection chamber 112. The analyte of interest (i.e., target analyte) within the interstitial fluid may bind to the capture antibody or to the enzyme-linked detection antibody. Once bound to one of the antibodies, the target analyte may bind to the other antibody, creating a "sandwich" on the electrode surface. In general, such sandwich configuration (i.e., a capture antibody binding to a target analyte that is also bound to an enzyme-linked detection antibody) may be referred to herein as an "Ab-analyte-Ab complex."

Upon formation of an Ab-analyte-Ab complex, the enzyme may catalyze a reaction using the substrate suspended in the hydrogel in proximity to the complex. In some embodiments, such enzymatic reactions may transfer electrons to the working electrode through the associated capture antibody. That is, electrons only reach the working electrode if the enzymatic reaction takes place in close proximity to a capture antibody bound to its surface (i.e., through formation of the Ab-analyte-Ab complex). In other embodiments, the enzymatic reaction may generate a reaction product that is reduced by electrons from the electrode. In such embodiments, electrons from the working electrode may also only be able to reduce the reaction product if the enzymatic reaction is carried out in close proximity to a capture antibody bound to its surface (i.e., through formation of the Ab-analyte-Ab complex).

Amperometric biosensors, including electrochemical biosensors that utilize amperometric detection exploit the current produced when an oxidation or reduction reaction occurs at an electrode. As such, the enzymes involved must have the ability to catalyze a reaction related to the presence of the target analyte, and that involves consumption of an electroactive reactant and/or the production of an electroactive product. The depletion or production process may be monitored amperometrically (i.e., the magnitude of current) and gives a direct indication of the analyte concentration.

Figure 4:
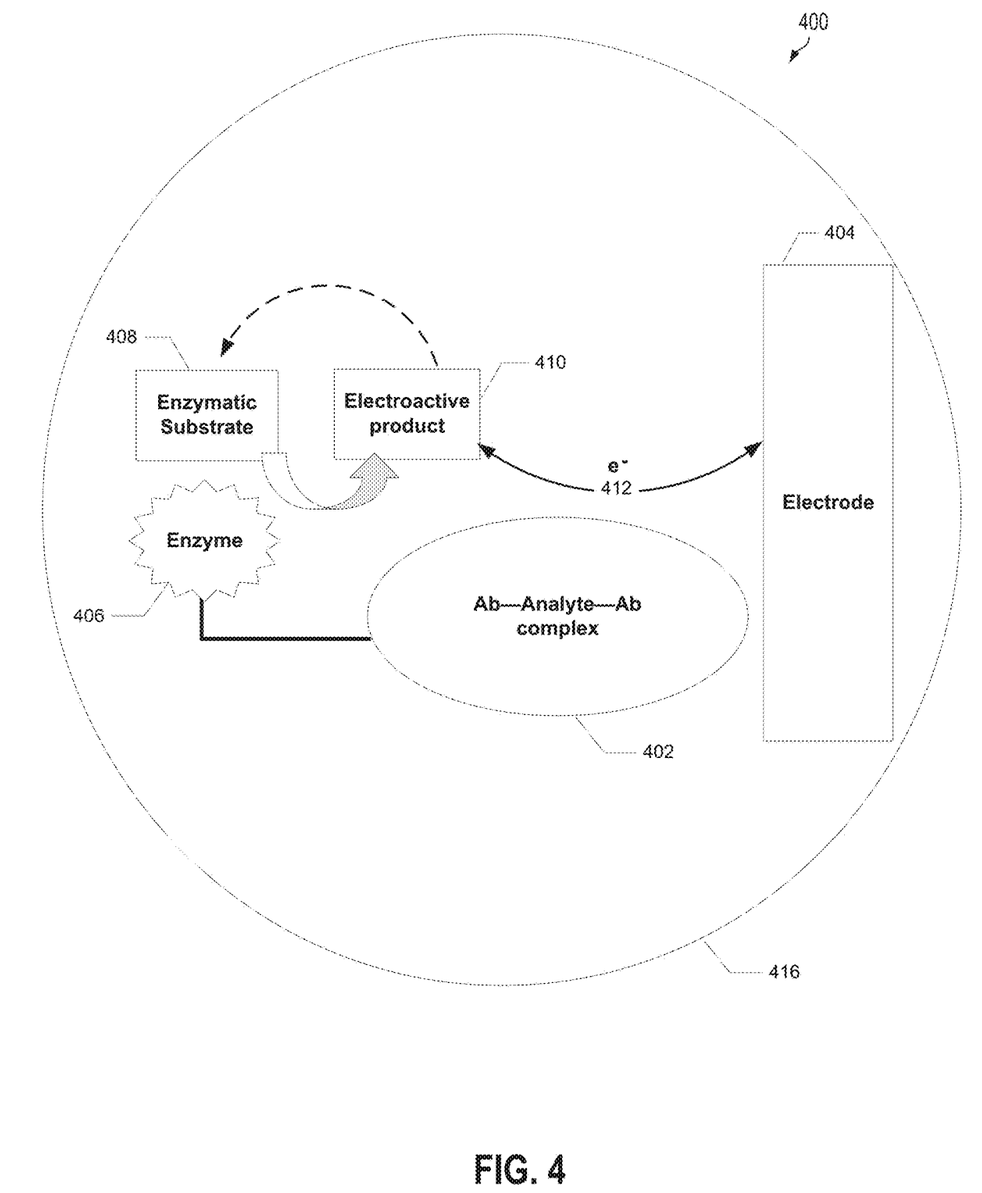
FIG. 4 is a schematic representation of enzymatic reactions that may be used to detect an analyte of interest in electrochemical bioassays of various embodiments.

FIG. 4 illustrates enzymatic reactions that may be enabled in sensing of a target analyte in various embodiment electrochemical bioassays and molecule detection assays. With reference to FIGS. 1A-4, a transdermal sensing and analysis device 400 may include a sensing chamber 416 with an electrochemical bioassay configured to detect the target analyte within the biological sample (e.g., interstitial fluid). Once the collected biological sample is provided to the sensing chamber 416, binding of the target analyte present in the sample to capture and detection antibodies creates Ab-analyte-Ab complexes 402 on the surface of an electrode 404 (e.g., a working electrode). In various embodiments, an enzyme 406 may be linked to the detection antibody. Molecules of an enzymatic substrate 408 within the sensing chamber may bind to the active site of the enzyme 406, catalyzing a reaction that generates an electroactive product 410. The nature of this reaction and the electroactive product may depend on the enzyme, the substrate, and the presence or absence of other reactive species, as discussed in further detail below.

In some embodiments, the electroactive product 410 may be a reduced form of an intermediate, substrate, cofactor, or mediator that can be oxidized by transferring electrons to the electrode 404. In other embodiments, the electroactive product 410 may be an oxidized form of an intermediate, substrate, cofactor, or mediator that can be reduced by electrons received from the electrode 404. The transfer of electrons to or from the electrode 404 in step 412 is enabled through the region of the electrode surface to which the capture Ab is bound, and therefore requires the enzyme to be linked to the Ab-analyte-Ab (as opposed to linked to an unbound detection antibody). In this manner, the electroactive product 410 may be oxidized or reduced by the electrode, which may regenerate (or be used to regenerate) the enzymatic substrate 408.

An example of the enzyme 406 that may be utilized in electrochemical bioassays according to the various embodiments is alkaline phosphatase (ALP). The corresponding enzyme substrate 408 may be phenyl phosphate. Specifically, ALP may catalyze decomposition of phenyl phosphate ($C_6H_5O_4P^{2-}$), through hydrolysis, generating phenol ($C_6H_6O$) and phosphate. The phosphate may combine with hydrogen ions in solution. This is shown in Eq. 1 below:

$$C_6H_5O_4P^{2-} + H_2O \xrightarrow{ALP} C_6H_6O + H_3PO_4 \quad \text{(Eq. 1)}$$

The resulting phenol may serve as an electroactive product 410. In the presence of an acidic medium, the phenol may be oxidized at an electrode surface, transferring electron(s) to the electrode (step 412) and generating one or more oxidation product (e.g., benzoquinone $C_6H_4O_2$). An example of this oxidation is shown in Eq. 2 below:

$$C_6H_6O + H_2O \xrightarrow{acid} C_6H_4O_2 + 4H^+ + 4e^- \quad \text{(Eq. 2)}$$

Thus for each molecule of phenol that is oxidized, four electrons may be transferred to the electrode (e.g., step 412). The ready oxidation of phenol may be due to the increased electron density in the benzene ring as a result of resonance, which enables easy electron removal at the hydroxyl group.

Since the electrons from phenol may only be passed to the electrode 404 through the Ab-analyte-Ab complex 402 to which the ALP is linked, the generated oxidation current may be proportional to the amount of analyte in the sample.

Other enzymes that may be utilized to generate a signal for amperometric detection require the presence of a redox cofactor. For example, an oxidized form of the redox cofactor (e.g., nicotinamide adenine dinucleotide ($NAD^{30}$), flavin adenine dinucleotide ($FAD^+$), etc.) may be the initial electron acceptor, and converted into a reduced form (e.g., NADH, $FADH_2$, etc.) during the reaction. In a typical reaction cycle using such an enzyme, a substrate ($X-H_2$) may bind to the enzyme active site and interact with the cofactor to generate an oxidized product (X) a, the reduced cofactor, and, in some reactions, $H^+$.

In some embodiments, the electrochemical bioassay may measure the amount of the reduced form of the cofactor that is generated during this catalytic breakdown of the substrate 408.

Other enzymes 406 that may be used in such electrochemical bioassays may include peroxidases, such as horseradish peroxidase (HRP) which is readily available in high purity at low cost. Specifically, HRP may catalyze electrochemical reduction of a substrate 408, which may be hydrogen peroxide ($H_2O_2$). For example, hydrogen peroxide in the solution may be reduced by HRP, or its associated cofactor (e.g., $Fe^{3+}$), generating an oxidized form of HRP/cofactor and $H_2O$. The oxidized form of the HRP/cofactor may be reduced by the electrons at the electrode surface (e.g., in step 412), leading to an increase in the reduction current.

Because of the large distance between the active sites of the HRP and the electrode surface, electron transfer from the electrode 404 may be indirectly accomplished using an electron mediator. That is, the HRP/cofactor may be regenerated by a mediator substance that serves as a reducing agent and becomes oxidized in the reaction. The oxidized mediator may then be electrochemically reduced by the electrode.

Electron mediators may also be employed in electrochemical bioassays that are based on reactions catalyzed by other enzymes. In some embodiments, a mediator may be reduced by the enzyme linked to the detection antibody, and the reduced form of the mediator may then be re-oxidized by transferring electrons to the electrode, thereby providing the amperometric signal.

Examples of electron mediators that may be used in conjunction with the enzyme in various embodiment electrochemical bioassays may include transition metal compounds, conducting polymers, and organic dyes. Transition metal compound-based mediators may include complexes with ferrocene (i.e., "Fc") ($Fe(C_5H_5)_2$), ferrocenecarboxaldehyde ($C_{11}H_{10}FeO$), ferricyanide ($Fe(CN)_6^{3-}$), Prussian blue, cobalt phthalocyanine, ruthenium phthalocyanine, osmium complexes with a variety of redox polymers (e.g., osmium bipyridyl complex ($C_{20}H_{16}C_{12}N_4O_5$)), or other transition metal compounds. Conducting polymer-based mediators may include poly(aniline)-poly(acrylate), poly(aniline)-poly(vinylsulfonate), poly(pyrrole), poly(pyrrole)-poly(vinylsulfonate), poly(vinylpyrrolidone), or other polymers. Organic dye-based mediators may include methylene green, Meldola blue, tetrathiafulvalene, thionine, tetracyanoquinodimethane (TCNQ), or quinine groups. In particular, mediators that may be incorporated for an HRP-catalyzed reaction include, without limitation, 3,3',5,5'-tetramethylbenzidine (TMB), o-phenylenediamine (OPD), hydroquinone (HQ), osmium complex, and phenol-based molecules (e.g., p-aminophenol, m-aminophenol, o-aminophenol (o-AP), etc.).

In various embodiments, a mediator(s) that facilitates the reaction catalyzed by HRP or other enzyme may be incorporated into the electrochemical bioassay by suspension in the hydrogel, similar to the enzymatic substrate.

Electrochemical bioassays according to the various embodiments may be used in transdermal sampling and analysis devices that detect a number of different medically relevant biomarkers, and therefore may have widespread clinical applications.

For example, cardiac troponin I (cTnI) is an important biomarker present in the blood stream within a few hours of an acute myocardial infarction (AMI). Small elevations in cTnI may also indicate a microscopic amount of myocardial necrosis. Therefore, detection of cTnI in a biological sample (e.g., interstitial fluid) may be utilized as an ultrasensitive biosensor for early detection or even prevention of a heart attack in at risk patients.

An electrochemical bioassay configured to detect cTnI as the target analyte may incorporate a pair of anti-troponin monoclonal antibodies (mAbs) that are generated using hybridoma techniques. For example, the 2B1.9 and 3D11.1 antibodies described in Bodor et al., "Development of monoclonal antibodies for an assay of cardiac troponin-I and preliminary results in suspected cases of myocardial infarction," Clin. Chem. 38(11):2203-14, 1992, may be used as capture and detection antibodies, respectively. In another example, the 9F5 and 2FL11 antibodies generated according to Wei et al., "A novel sandwich immunosensing method for measuring cardiac troponin I in sera," Anal Biochem. 321(2):209-16, Oct. 15, 2003, may be used as capture and detection antibodies, respectively.

In other embodiments, combinations of anti-cTnI mAbs may be used to improve binding affinity, such as two or more capture antibodies on the electrode surface and two or more detection antibodies linked to an enzyme and suspended in the hydrogel.

Melatonin is an important hormone for monitoring sleep patterns and/or sleep disfunction, and influencing physiological processes (e.g., reproduction, immune regulation, aging, etc.). Further, the measurement of melatonin in body fluid, such as interstitial fluid, may be used to evaluate pineal function. Therefore, an electrochemical bioassay may be configured in a transdermal sampling and analysis device to detect the amount of melatonin. In some embodiments, melatonin-hemisuccinate-human serum may be bound to the electrode surface instead of a capture antibody, and a peroxidase-linked anti-melatonin IgG antibody may be used as the enzyme-linked detection antibody, prepared as described in de Almedia et al., "Measurement of melatonin in body fluids: standards, protocols and procedures," Childs Nery Syst. 27(6):878-91, June 2011.

Electrochemical bioassays in various embodiments may also be developed to detect biomarkers of bacterial infections in order to distinguish them from viral or fungal infections, as well as measure the severity of bacterial infections. Such biomarkers may include, among others, procalcitonin (PCT), heparin-binding protein (HBP), and interleukin-6 (IL-6). In various embodiments, an electrochemical bioassay may be configured to detect a bacterial infection biomarker from a biological sample (e.g., interstitial fluid) in a transdermal sampling and analysis device. In particular, for detection and analysis of PCT, the electrochemical bioassay may utilize as the respective capture and detection antibodies two different monoclonal rat antibodies directed against human PCT, such as rat anti-human CALCA clones 4A6 and 42F3 (referenced in Yanez et al., "Development and validation of an ultrasensitive procalcitonin sandwich immunoassay," High-Throughput 6(4):18, 2017). For detection and analysis of HBP, the electrochemical bioassay may utilize a mouse monoclonal anti-HBP antibody (2F23A) as the capture antibody, and purified IgG from a polyclonal anti-HBP rabbit serum as the detection antibody (referenced in Linder et al., "Heparin-binding protein: an early marker of circulatory failure in sepsis," Clinical Infectious Diseases 49(7):1044-50, Oct. 1, 2009).

For detection and analysis of IL-6, the electrochemical bioassay may utilize an anti-IL-6 receptor mAb (e.g., MT-18) as the capture antibody, and biotinylated guinea pig anti-IL-6 receptor Ab (e.g., αGV6R) as the detection antibody (referenced in Mitsuyama et al., "Soluble interleukin-6 receptors in inflammatory bowel disease: relation to circulating interleukin-6," Gut 36:45-9, 1995).

Cortisol may be analyzed to indicate the level of a patient's physical or mental stress, and may be elevated during times of extreme anxiety, due to mental illness, or during a viral or bacterial infection. Therefore, an electrochemical bioassay may be configured to detect the amount of cortisol in a biological sample (e.g., interstitial fluid) within an embodiment transdermal sampling and analysis device.

Figure 5A:
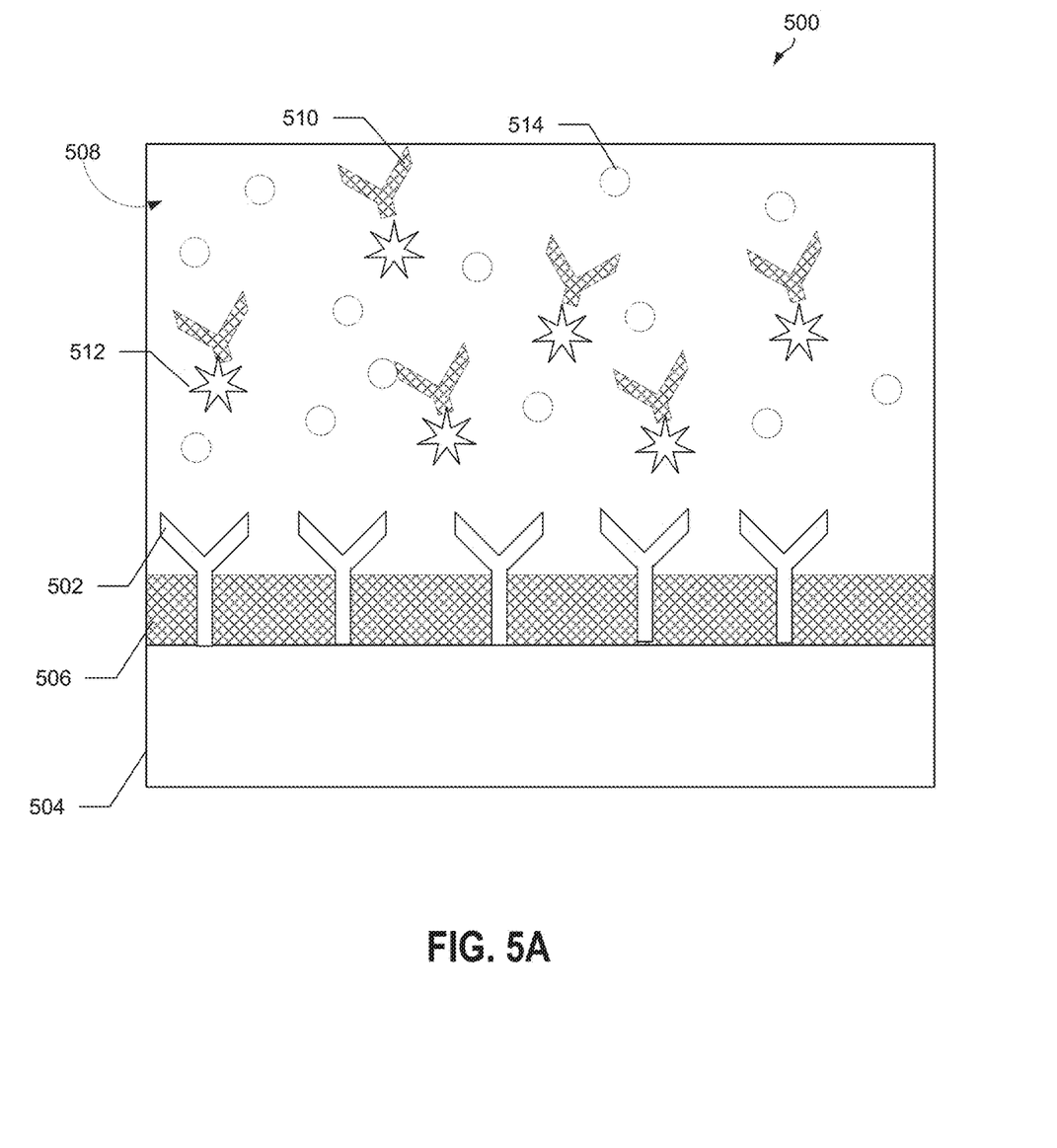
FIGS. 5A and 5B are schematic illustrations of an embodiment electrochemical bioassay in a transdermal sampling and analysis device.

FIG. 5A illustrates the composition of an example electrochemical bioassay 500 that quantifies the amount of a target analyte based on the oxidation current generated. With reference to FIGS. 1A-5A, a capture antibody 502 having a high affinity for the target analyte may be bound to the surface of an electrode 504 (e.g., a working electrode) in a transdermal sensing and analysis device. For example, the target analyte may be cTnI, and an anti-cTnI mAb may be selected as the high affinity capture antibody 502. In some embodiments, the capture antibody 502 may be a single type/species, while in other embodiments the capture antibody 502 may include a combination of a multiple antibodies that each have an affinity for the target analyte. species may Additionally, the electrochemical bioassay 500 may include at least one electrode barrier layer 506 (e.g., BSA) applied to the surface of the electrode 504.

In the embodiments, a hydrogel 508 may be applied over the electrode barrier layer 506 and the capture antibody 502 bound to the surface of the electrode 504. Embedded within the hydrogel 508 may be a detection antibody 510 conjugated to an enzyme 512. A corresponding enzymatic substrate 514 may also be suspended in the hydrogel 508.

In some embodiments, the detection antibody 510 may be an anti-cTnI mAb that is different from the capture antibody 502, and therefore binds a different site on cTnI. Similar to the capture antibody 502, the detection antibody 510 may be a single type/species, or may be a combination of a multiple antibodies that each have an affinity for the target analyte. In some embodiments, the enzyme 512 may be ALP and the enzymatic substrate 514 may be phenyl phosphate, as described in further detail above.

Figure 5B:
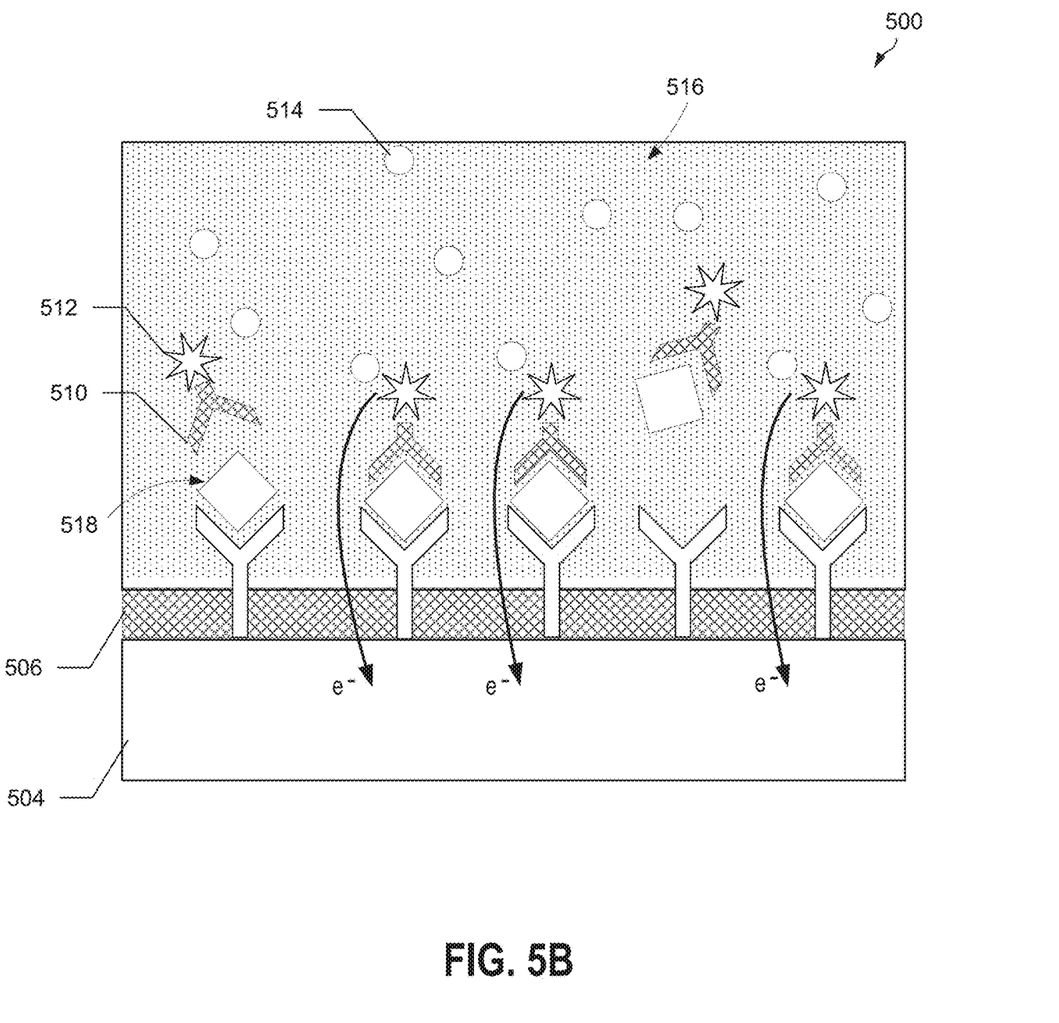

FIG. 5B illustrates the components of the electrochemical bioassay 500 during use on a subject. With reference to FIGS. 1A-5B, sample of interstitial fluid 516 that has been collected may be introduced to the area occupied by the hydrogel 508 (i.e., within the sensing chamber). In various embodiments, the target analyte 518 (e.g., cTnI) in the interstitial fluid 516 may bind to the capture antibody 502 or the detection antibody 510, followed by binding of the other antibody i.e., detection antibody 510 or capture antibody 502) to the target analyte 518. In this manner, Ab-analyte-Ab complexes may be created on the surface of the electrode 504.

In various embodiments, the enzyme 512 (e.g., ALP) that is linked to the detection antibody 510 may catalyze a reaction involving the enzymatic substrate 514 (e.g., phenyl phosphate) n the hydrogel. In various embodiments, the enzymatic reaction may generate an electroactive product (e.g., phenol) that can transfer electrons to the electrode 504. As a result of the electrode barrier layer 506, such electron transfer may only occur at the bound capture electrode 502. Therefore, electrons may only be transferred to the electrode 504 if the detection antibody 510 to which the catalyzing enzyme 512 is linked is bound to the target analyte 518 (i.e., in an Ab-analyte-Ab complex). In this manner, the amount of electron transfer to the electrode 508 directly corresponds to the amount of the target analyte 516 bound to antibodies in the electrochemical bioassay 500, and may provide a measure of the amount of target analyte 516 within the collected interstitial fluid 518.

While discussed with respect to cTnI, the electrochemical bioassay 500 may be modified to detect any of a number of target analytes. Further, while referred to herein as capture and detection antibodies, pairs or groups of other types of small molecule linkers may be employed in the embodiment electrochemical assays, such as aptamers and/or affimers.

In some embodiments, the electrode barrier layer (e.g., 506) may be charged, and may be associated with the electrode using a variety of forces, such as charge interaction, covalent bonding, van der Waals forces, etc. In various embodiments, the at least one electrode barrier layer may be formed using a variety of materials, including but not limited to BSA, alginates, or other anionic naturally occurring polymers. Such materials may be applied to the electrode using processes that include, but are not limited to, chemical and physical deposition processes.

Parameters for creating the sensing element according to the various embodiments, including materials, concentration, temperature, and time, may be adjusted based on the analyte of interest.

The transdermal sampling and analysis devices of the various embodiments may be manufactured using different methods and materials. Manufacturing methods for an embodiment transdermal sampling and analysis device may be disclosed in the related International Application Number PCT/US2006/023194, filed Jun. 14, 2006, entitled "Flexible Apparatus and Method for Monitoring and Delivery," which claims priority to the International Application Number PCT/US2005/044287, entitled "Apparatus and Method for Continuous Real-Time Trace Bimolecular Sampling, Analysis and Deliver," filed on Dec. 9, 2005. The manufacture of an embodiment transdermal sampling and analysis device 100, 200, 300, is also disclosed in the publication entitled "Novel Non-Intrusive Trans-Dermal Remote Wireless Micro-Fluidic Monitoring System Applied to Continuous Glucose and Lactate Assays for Casualty and Combat Readiness Assessment" by John F. Currie, Michael M. Bodo and Frederick J. Pearce, RTO-MP-HFM-109:24-1, Aug. 16, 2004. The entire contents of these related applications and the publication are incorporated by reference herein.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

While the invention has been described in detail with respect to specific embodiments thereof, it will be apparent to those skilled in the art that various alterations, modifications and other changes may be made without departing from the scope of the embodiments described herein. It is therefore intended that all such modifications, alterations and other changes be encompassed by the claims. Further, any reference to claim elements in the singular, for example, using the articles "a," "an" or "the" is not to be construed as limiting the element to the singular.

What is claimed is:

1. A transdermal sampling and analysis device comprising:
    a substrate;
    at least one disruptor mounted on the substrate, wherein the at least one disruptor is configured to generate a localized heat capable of altering permeability characteristics of a stratum corneum layer of skin of an organism;
    a reservoir configured to collect and contain a biological sample;
    at least two electrodes; and
    an electrochemical bioassay configured to determine levels of a target analyte in the biological sample, wherein the electrochemical bioassay comprises:
        a first small molecule binding element bound to a surface of at least one of the electrodes;
        at least one barrier layer covering a remainder of the surface such that the entire surface is either occupied by a bound first small molecule binding element or covered by the barrier layer, wherein the at least one barrier layer comprises an alginate; and
        a second small molecule binding element linked to an enzyme, wherein the second small molecule binding element, the linked enzyme, and at least one substrate of the linked enzyme are suspended in a hydrogel on top of the at least one of the electrodes.

2. The transdermal sampling and analysis device of claim 1, wherein the target analyte is selected from the group consisting of cardiac troponin I (cTnI), melatonin, procalcitonin (PCT), heparin-binding protein (HBP), and interleukin-6 (IL-6).

3. The transdermal sampling and analysis device of claim 1, wherein the target analyte is a small molecule that includes at least one binding site for each of the first small molecule binding element and the second small molecule binding element.

4. The transdermal sampling and analysis device of claim 1, wherein the linked enzyme catalyzes a reaction of the at least one substrate, wherein the reaction causes transfer of electrons to the at least one of the electrodes when carried out in proximity to the first small molecule binding element.

5. The transdermal sampling and analysis device of claim 1, wherein the first and second small molecule binding elements comprise antibodies, aptamers, or affimers.

6. The transdermal sampling and analysis device of claim 1, wherein:
    the linked enzyme is selected from the group consisting of alkaline phosphatase (ALP) and horseradish peroxidase (HRP); and
    the substrate of the linked enzyme is selected from the group consisting of phenyl phosphate and hydrogen peroxide.

7. The transdermal sampling and analysis device of claim 1, wherein:
    the electrochemical bioassay further comprises an electron mediator suspended in the hydrogel, wherein the electron mediator is selected from the group consisting of ferrocene, osmium bipyridine complexes, ruthenium phthalocyanine complexes, quinone, tetrathialfulvalene (TTF), tetracyanoquinodimethane (TCNQ), and thionine.

8. The transdermal sampling and analysis device of claim 1, wherein at least one of the first and second small molecule binding elements comprises a combination of two or more antibodies configured to bind different epitopes of the target analyte.

9. The transdermal sampling and analysis device of claim 1, wherein the biological sample is interstitial fluid (ISF).

10. A method for using a transdermal sampling and analysis device to detect a target analyte in a biological sample, the method comprising:
    providing a localized heat capable of altering permeability characteristics of a stratum corneum layer of skin of an organism, wherein the localized heat is generated by at least one disruptor mounted on a substrate of the transdermal sampling and analysis device;
    collecting and containing a biological sample within a reservoir of the transdermal sampling and analysis device; and
    determining levels of the target analyte in the biological sample using an electrochemical bioassay, wherein the electrochemical bioassay comprises:
        a first small molecule binding element bound to a surface of at least one electrode of the transdermal sampling and analysis device;
        at least one barrier layer covering a remainder of the surface such that the entire surface is either occupied by a bound first small molecule binding element or covered by the barrier layer, wherein the at least one barrier layer comprises an alginate; and
        a second small molecule binding element linked to an enzyme, wherein the second small molecule binding element, the linked enzyme, and at least one substrate of the linked enzyme are suspended in a hydrogel on top of the at least one electrode.

11. The method of claim 10, wherein the target analyte is selected from the group consisting of cardiac troponin I (cTnI), melatonin, procalcitonin (PCT), heparin-binding protein (HRP), and interleukin-6 (IL-6).

12. The method of claim 10, wherein the target analyte is a small molecule that includes at least one binding site for each of the first small molecule binding element and the second small molecule binding element.

13. The method of claim 10, wherein the linked enzyme catalyzes a reaction of the at least one substrate, wherein the reaction causes transfer of electrons to the at least one electrode when carried out in proximity to the first small molecule binding element.

14. The method of claim 10, wherein the first and second small molecule binding elements comprise antibodies, aptamers, or affimers.

15. The method of claim 10, wherein:
    the linked enzyme is selected from the group consisting of alkaline phosphatase (ALP) and horseradish peroxidase (HRP); and
    the substrate of the linked enzyme is selected from the group consisting of phenyl phosphate and hydrogen peroxide.

16. The method of claim 10, wherein:
the electrochemical bioassay further comprises an electron mediator suspended in the hydrogel, wherein the electron mediator is selected from the group consisting of ferrocene, osmium bipyridine complexes, ruthenium phthalocyanine complexes, quinone, tetrathialfulvalene (TTF), tetracyanoquinodimethane (TCNQ), and thionine.

17. The method of claim 10, wherein at least one of the first and second small molecule binding elements comprises a combination of two or more antibodies configured to bind different epitopes of the target analyte.

18. The method of claim 10, wherein the biological sample is interstitial fluid (ISF).

\* \* \* \* \*